(12) United States Patent
Malinowski

(10) Patent No.: US 10,436,808 B2
(45) Date of Patent: Oct. 8, 2019

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Michal Malinowski, Bietigheim-Bissingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/840,805

(22) Filed: Dec. 13, 2017

(65) Prior Publication Data

US 2018/0188280 A1 Jul. 5, 2018

(30) Foreign Application Priority Data

Dec. 29, 2016 (EP) .................................... 16207353

(51) Int. Cl.
| | |
|---|---|
| *G01N 35/10* | (2006.01) |
| *G01N 35/04* | (2006.01) |
| *H01F 7/02* | (2006.01) |
| *G01B 7/00* | (2006.01) |
| *G01N 35/00* | (2006.01) |

(52) U.S. Cl.
CPC ......... *G01N 35/1081* (2013.01); *G01N 35/04* (2013.01); *H01F 7/0205* (2013.01); *G01B 7/003* (2013.01); *G01N 2035/00425* (2013.01); *G01N 2035/0406* (2013.01); *G01N 2035/0422* (2013.01); *G01N 2035/0477* (2013.01); *G01N 2035/0491* (2013.01); *G01N 2035/0493* (2013.01)

(58) Field of Classification Search
CPC combination set(s) only.
See application file for complete search history.

(56) References Cited

U.S. PATENT DOCUMENTS

| | | | |
|---|---|---|---|
| 3,273,727 | A | 9/1966 | Rogers et al. |
| 3,653,485 | A | 4/1972 | Donlon |
| 3,901,656 | A | 8/1975 | Durkos et al. |
| 4,150,666 | A | 4/1979 | Brush |
| 4,395,164 | A | 7/1983 | Beltrop et al. |
| 4,544,068 | A | 10/1985 | Cohen |
| 4,771,237 | A | 9/1988 | Daley |
| 5,120,506 | A | 6/1992 | Saito et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Kyle O Logan
(74) *Attorney, Agent, or Firm* — Roche Diagnostics Operations, Inc.

(57) ABSTRACT

A laboratory sample distribution system is presented. The system comprises a number of sample container carriers, a transport plane, a number of electro-magnetic actuators, a number of position sensors and a position determination unit. The position sensors and the position determination unit enable improved sample container carrier position detection on the transport plane. A laboratory automation system comprising such a laboratory sample distribution system is also presented.

14 Claims, 2 Drawing Sheets

(56) References Cited

U.S. PATENT DOCUMENTS

| | | | |
|---|---|---|---|
| 5,216,363 A * | 6/1993 | Masaaki | G01B 7/003 324/207.21 |
| 5,295,570 A | 3/1994 | Grecksch et al. | |
| 5,309,049 A | 5/1994 | Kawada et al. | |
| 5,442,865 A | 8/1995 | Wallrafen | |
| 5,457,368 A * | 10/1995 | Jacobsen | G01B 7/003 200/11 R |
| 5,523,131 A | 6/1996 | Isaacs et al. | |
| 5,530,345 A | 6/1996 | Murari et al. | |
| 5,636,548 A | 6/1997 | Dunn et al. | |
| 5,641,054 A | 6/1997 | Mori et al. | |
| 5,651,941 A | 7/1997 | Stark et al. | |
| 5,720,377 A | 2/1998 | Lapeus et al. | |
| 5,735,387 A | 4/1998 | Polaniec et al. | |
| 5,788,929 A | 8/1998 | Nesti | |
| 5,798,640 A | 8/1998 | Gier et al. | |
| 6,045,319 A | 4/2000 | Uchida et al. | |
| 6,062,398 A | 5/2000 | Thalmayr | |
| 6,070,337 A | 6/2000 | Wallrafen | |
| 6,141,602 A | 10/2000 | Igarashi et al. | |
| 6,151,535 A | 11/2000 | Ehlers | |
| 6,184,596 B1 | 2/2001 | Ohzeki | |
| 6,191,507 B1 | 2/2001 | Peltier et al. | |
| 6,206,176 B1 | 3/2001 | Blonigan et al. | |
| 6,255,614 B1 | 7/2001 | Yamakawa et al. | |
| 6,260,360 B1 | 7/2001 | Wheeler | |
| 6,279,728 B1 | 8/2001 | Jung et al. | |
| 6,293,750 B1 | 9/2001 | Cohen et al. | |
| 6,429,016 B1 | 8/2002 | McNeil | |
| 6,444,171 B1 | 9/2002 | Sakazume et al. | |
| 6,571,934 B1 | 6/2003 | Thompson et al. | |
| 7,028,831 B2 | 4/2006 | Veiner | |
| 7,078,082 B2 | 7/2006 | Adams | |
| 7,122,158 B2 | 10/2006 | Itoh | |
| 7,278,532 B2 | 10/2007 | Martin | |
| 7,326,565 B2 | 2/2008 | Yokoi et al. | |
| 7,425,305 B2 | 9/2008 | Itoh | |
| 7,428,957 B2 | 9/2008 | Schaefer | |
| 7,578,383 B2 | 8/2009 | Itoh | |
| 7,597,187 B2 | 10/2009 | Bausenwein et al. | |
| 7,850,914 B2 | 12/2010 | Veiner et al. | |
| 7,858,033 B2 | 12/2010 | Itoh | |
| 7,875,254 B2 | 1/2011 | Garton et al. | |
| 7,939,484 B1 | 5/2011 | Loeffler et al. | |
| 8,240,460 B1 | 8/2012 | Bleau et al. | |
| 8,281,888 B2 | 10/2012 | Bergmann | |
| 8,502,422 B2 | 8/2013 | Lykkegaard | |
| 8,796,186 B2 | 8/2014 | Shirazi | |
| 8,833,544 B2 | 9/2014 | Stoeckle et al. | |
| 8,973,736 B2 | 3/2015 | Johns et al. | |
| 9,097,691 B2 | 8/2015 | Onizawa et al. | |
| 9,187,268 B2 | 11/2015 | Denninger et al. | |
| 9,211,543 B2 | 12/2015 | Ohga et al. | |
| 9,239,335 B2 | 1/2016 | Heise et al. | |
| 9,423,410 B2 | 8/2016 | Buehr | |
| 9,423,411 B2 | 8/2016 | Riether | |
| 9,567,167 B2 | 2/2017 | Sinz | |
| 9,575,086 B2 | 2/2017 | Heise et al. | |
| 9,593,970 B2 | 3/2017 | Sinz | |
| 9,598,243 B2 | 3/2017 | Denninger et al. | |
| 9,618,525 B2 | 4/2017 | Malinowski et al. | |
| 9,658,241 B2 | 5/2017 | Riether et al. | |
| 9,664,703 B2 | 5/2017 | Heise et al. | |
| 9,772,342 B2 | 9/2017 | Riether | |
| 9,791,468 B2 | 10/2017 | Riether et al. | |
| 9,810,706 B2 | 11/2017 | Riether et al. | |
| 2002/0009391 A1 | 1/2002 | Marquiss et al. | |
| 2003/0092185 A1 | 5/2003 | Qureshi et al. | |
| 2004/0050836 A1 | 3/2004 | Nesbitt et al. | |
| 2004/0084531 A1 | 5/2004 | Itoh | |
| 2005/0061622 A1 | 3/2005 | Martin | |
| 2005/0109580 A1 | 5/2005 | Thompson | |
| 2005/0194333 A1 | 9/2005 | Veiner et al. | |
| 2005/0196320 A1 | 9/2005 | Veiner et al. | |
| 2005/0226770 A1 | 10/2005 | Allen et al. | |
| 2005/0242963 A1 | 11/2005 | Oldham et al. | |
| 2005/0247790 A1 | 11/2005 | Itoh | |
| 2005/0260101 A1 | 11/2005 | Nauck et al. | |
| 2005/0271555 A1 | 12/2005 | Itoh | |
| 2006/0000296 A1 | 1/2006 | Salter | |
| 2006/0047303 A1 | 3/2006 | Ortiz et al. | |
| 2006/0219524 A1 | 10/2006 | Kelly et al. | |
| 2007/0116611 A1 | 5/2007 | DeMarco | |
| 2007/0210090 A1 | 9/2007 | Sixt et al. | |
| 2007/0248496 A1 | 10/2007 | Bondioli et al. | |
| 2007/0276558 A1 | 11/2007 | Kim | |
| 2008/0012511 A1 | 1/2008 | Ono | |
| 2008/0029368 A1 | 2/2008 | Komori | |
| 2008/0056328 A1 | 3/2008 | Rund et al. | |
| 2008/0131961 A1 | 6/2008 | Crees et al. | |
| 2009/0004117 A1 | 1/2009 | LaBarre et al. | |
| 2009/0022625 A1 | 1/2009 | Lee et al. | |
| 2009/0081771 A1 | 3/2009 | Breidford et al. | |
| 2009/0128139 A1 | 5/2009 | Drenth et al. | |
| 2009/0142844 A1 | 6/2009 | Le Comte | |
| 2009/0180931 A1 | 7/2009 | Silbert et al. | |
| 2009/0322486 A1 | 12/2009 | Gerstel | |
| 2010/0000250 A1 | 1/2010 | Sixt | |
| 2010/0033167 A1 | 2/2010 | Peter | |
| 2010/0152895 A1 | 6/2010 | Dai | |
| 2010/0175943 A1 | 7/2010 | Bergmann | |
| 2010/0186618 A1 | 7/2010 | King et al. | |
| 2010/0255529 A1 | 10/2010 | Cocola et al. | |
| 2010/0300831 A1 | 12/2010 | Pedrazzini | |
| 2010/0312379 A1 | 12/2010 | Pedrazzini | |
| 2011/0050213 A1 | 3/2011 | Furukawa | |
| 2011/0101966 A1 | 5/2011 | Dengler et al. | |
| 2011/0124038 A1 | 5/2011 | Bishop et al. | |
| 2011/0172128 A1 | 7/2011 | Davies et al. | |
| 2011/0186406 A1 | 8/2011 | Kraus et al. | |
| 2011/0287447 A1 | 11/2011 | Norderhaug et al. | |
| 2012/0037696 A1 | 2/2012 | Lavi | |
| 2012/0129673 A1 | 5/2012 | Fukugaki et al. | |
| 2012/0178170 A1 | 7/2012 | Van Praet | |
| 2012/0211645 A1 | 8/2012 | Tullo et al. | |
| 2012/0275885 A1 | 11/2012 | Furrer et al. | |
| 2012/0282683 A1 | 11/2012 | Mototsu | |
| 2012/0295358 A1 | 11/2012 | Ariff et al. | |
| 2012/0310401 A1 | 12/2012 | Shah | |
| 2013/0034410 A1 | 2/2013 | Heise et al. | |
| 2013/0153677 A1 | 6/2013 | Leen et al. | |
| 2013/0180824 A1 | 7/2013 | Kleinikkink et al. | |
| 2013/0263622 A1 | 10/2013 | Mullen et al. | |
| 2013/0322992 A1 | 12/2013 | Pedrazzini | |
| 2014/0170023 A1 | 6/2014 | Saito et al. | |
| 2014/0234949 A1 | 8/2014 | Wasson et al. | |
| 2014/0234978 A1 * | 8/2014 | Heise | B65G 54/02 436/48 |
| 2015/0014125 A1 | 1/2015 | Hecht | |
| 2015/0166265 A1 | 6/2015 | Pollack et al. | |
| 2015/0241457 A1 | 8/2015 | Miller | |
| 2015/0273468 A1 | 10/2015 | Croquette et al. | |
| 2015/0273691 A1 | 10/2015 | Pollack | |
| 2015/0276775 A1 | 10/2015 | Mellars et al. | |
| 2015/0276782 A1 | 10/2015 | Riether | |
| 2016/0003859 A1 | 1/2016 | Wenczel et al. | |
| 2016/0025756 A1 | 1/2016 | Pollack et al. | |
| 2016/0054341 A1 | 2/2016 | Edelmann | |
| 2016/0077120 A1 | 3/2016 | Riether | |
| 2016/0229565 A1 | 8/2016 | Margner | |
| 2016/0274137 A1 | 9/2016 | Baer | |
| 2016/0282378 A1 | 9/2016 | Malinowski et al. | |
| 2016/0341750 A1 | 11/2016 | Sinz et al. | |
| 2016/0341751 A1 | 11/2016 | Huber et al. | |
| 2017/0059599 A1 | 3/2017 | Riether | |
| 2017/0096307 A1 | 4/2017 | Mahmudimanesh et al. | |
| 2017/0097372 A1 | 4/2017 | Heise et al. | |
| 2017/0101277 A1 | 4/2017 | Malinowski | |
| 2017/0108522 A1 | 4/2017 | Baer | |
| 2017/0131307 A1 | 5/2017 | Pedain | |
| 2017/0131309 A1 | 5/2017 | Pedain | |
| 2017/0131310 A1 | 5/2017 | Volz et al. | |
| 2017/0138971 A1 | 5/2017 | Heise et al. | |
| 2017/0160299 A1 | 6/2017 | Schneider et al. | |

(56) References Cited

U.S. PATENT DOCUMENTS

| | | |
|---|---|---|
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0217174 A1 | 8/2018 | Malinowski |
| 2018/0217176 A1 | 8/2018 | Sinz et al. |
| 2018/0224476 A1 | 8/2018 | Birrer et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S62-234780 A | 10/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 8/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

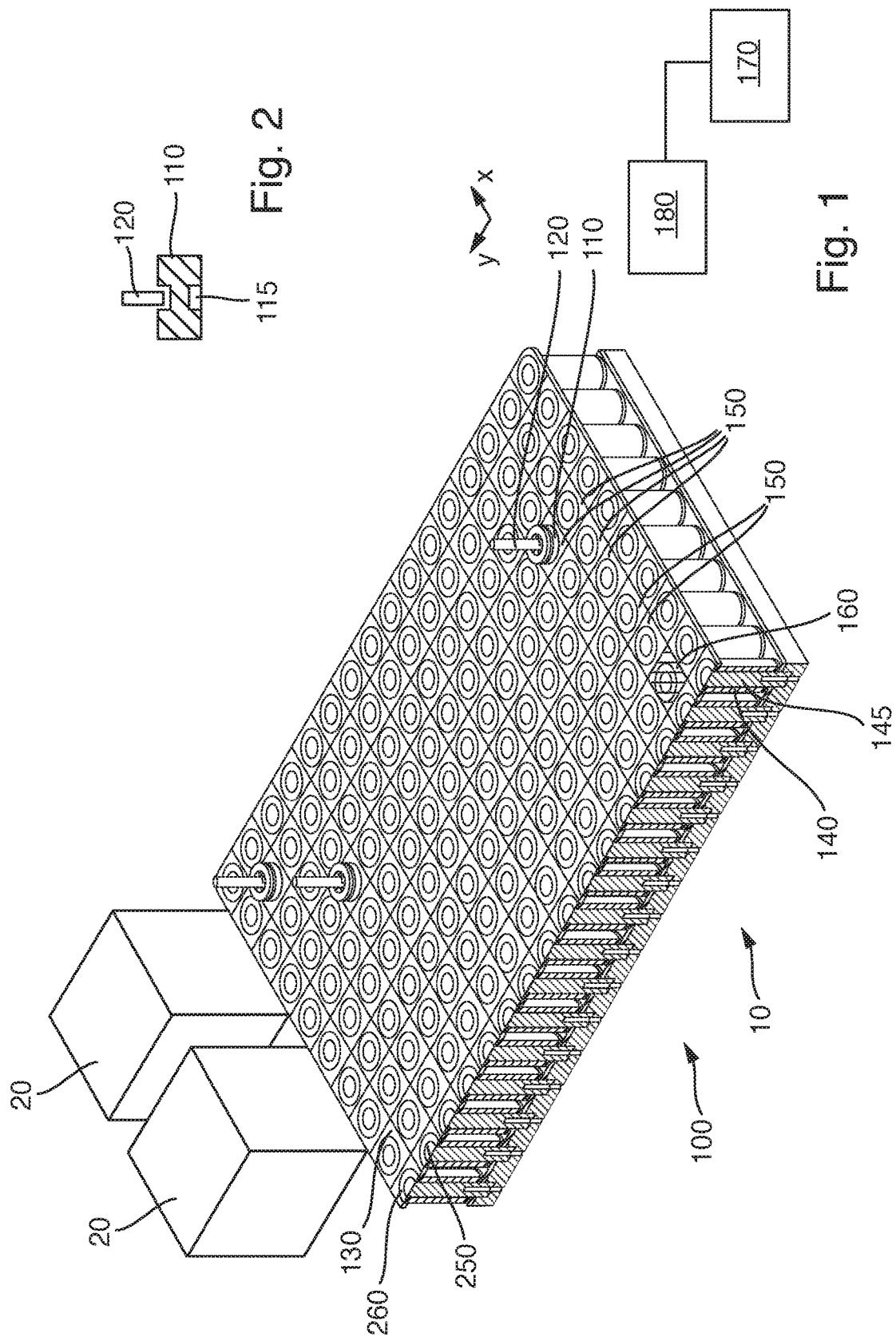

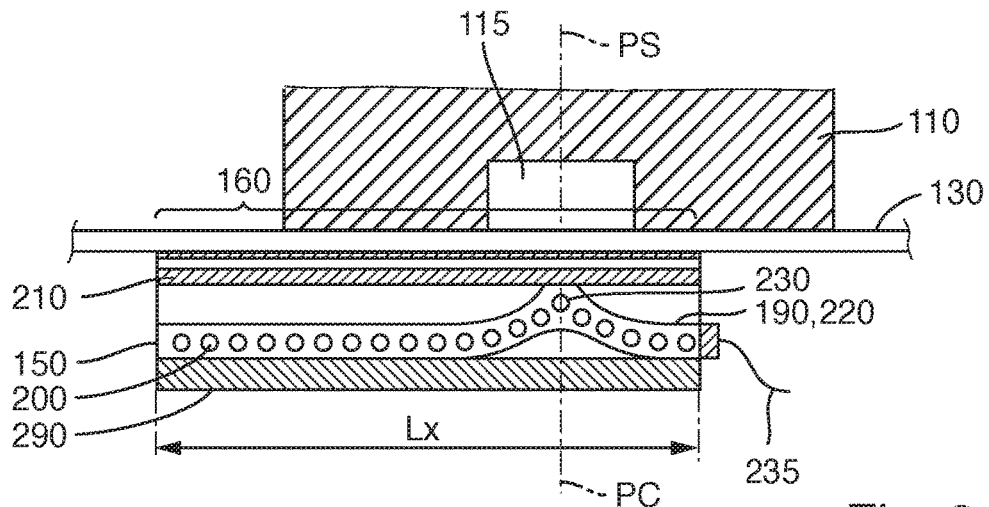
Fig. 3
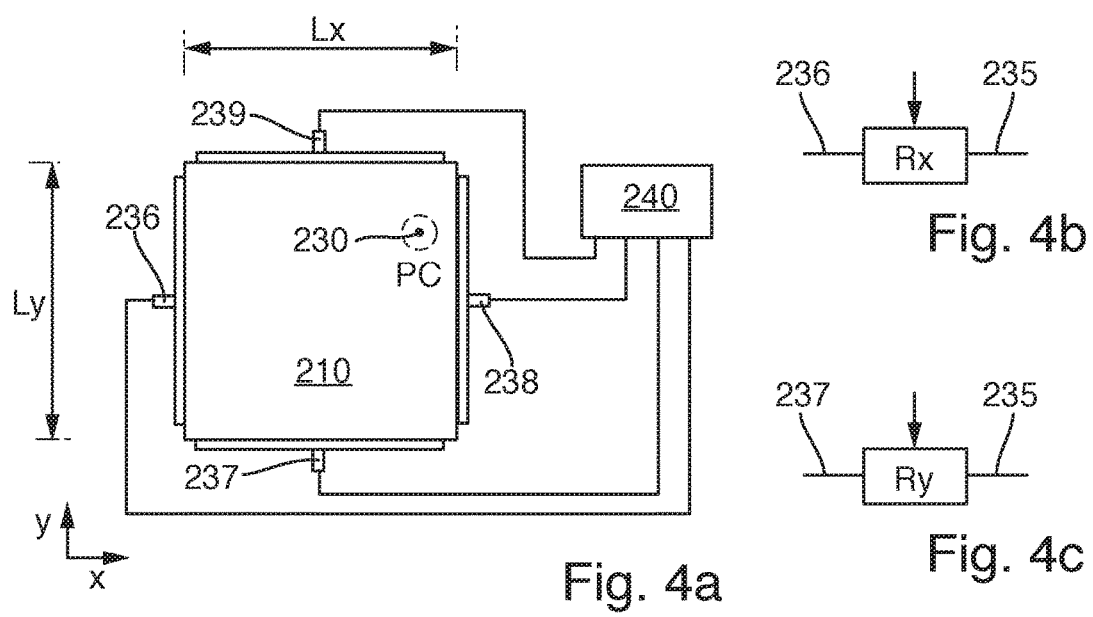
Fig. 4a
Fig. 4b
Fig. 4c
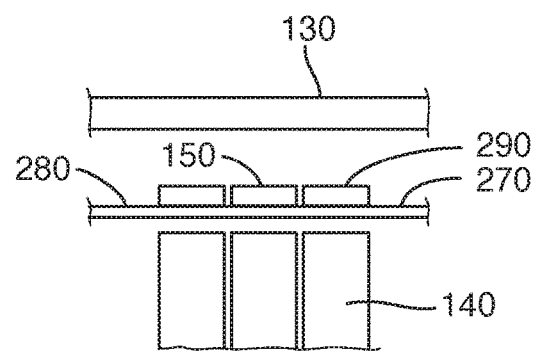
Fig. 5

LABORATORY SAMPLE DISTRIBUTION SYSTEM AND LABORATORY AUTOMATION SYSTEM

CROSS-REFERENCE TO RELATED APPLICATIONS

This application is based on and claims priority to EP 16207353.0, filed Dec. 29, 2016, which is hereby incorporated by reference.

BACKGROUND

The present disclosure relates to a laboratory sample distribution system and a laboratory automation system.

Known laboratory sample distribution systems are typically used in laboratory automation systems in order to distribute samples contained in sample containers between different laboratory stations by means of sample container carriers. Such systems use Hall-sensors for detecting positions of sample container carriers on a transport plane.

Therefore, there is a need for a laboratory sample distribution system having an improved sample container carrier position detection than laboratory sample distribution systems of the prior art.

SUMMARY

According to the present disclosure, a laboratory sample distribution system is presented. The laboratory sample distribution system can comprise a number of sample container carriers. Each of the sample container carriers can comprise at least one magnetically active device and each of the sample container carriers can be adapted to carry at least one sample container. The laboratory sample distribution system can also comprise a transport plane. The transport plane can be adapted to support the sample container carriers. The laboratory sample distribution system can also comprise a number of electro-magnetic actuators. The electro-magnetic actuators can be stationary arranged below the transport plane. The electro-magnetic actuators can be adapted to move the sample container carriers on top of the transport plane by applying magnetic move forces to the sample container carriers. The laboratory sample distribution system can also comprise a number of position sensors. The position sensors can be stationary arranged below the transport plane. A position sensor can have a sensing region and an electrical resistance (Rx, Ry). The electrical resistance can be dependent on a position (PS) of a sample container carrier on the transport plane located in the sensing region. The laboratory sample distribution system can also comprise a position determination unit. The position determination unit can be adapted to determine the positions of the sample container carriers on top of the transport plane by evaluating the electrical resistances of the position sensors.

Accordingly, it is a feature of the embodiments of the present disclosure to provide a laboratory sample distribution system having an improved sample container carrier position detection than laboratory sample distribution systems of the prior art. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a perspective view of a laboratory automation system comprising a laboratory sample distribution system according to an embodiment of the present disclosure.

FIG. 2 illustrates a longitudinal section view of a sample container carrier of FIG. 1 according to an embodiment of the present disclosure.

FIG. 3 illustrates a longitudinal section view of a sample container carrier, a transport plane and a position sensor of FIG. 1 according to an embodiment of the present disclosure.

FIG. 4a illustrates a cross section view of the position sensor of FIG. 3 according to an embodiment of the present disclosure.

FIG. 4b illustrates an electronic symbol for the position sensor of FIG. 3 in a first direction according to an embodiment of the present disclosure.

FIG. 4c illustrates another electronic symbol for the position sensor of FIG. 3 in a second direction according to an embodiment of the present disclosure.

FIG. 5 illustrates a longitudinal section view of the laboratory sample distribution system of FIG. 1 according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is disclosed. The system can comprise a number of sample container carriers, a transport plane and a number of electro-magnetic actuators. Each of the sample container carriers can comprise at least one magnetically active device. Also, each of the sample container carriers can be adapted to carry at least one sample container. The transport plane can be adapted to support the sample container carriers. The electro-magnetic actuators can be stationary arranged below the transport plane. Furthermore, the electro-magnetic actuators can be adapted to move the sample container carriers on top of the transport plane, in particular each of them along an individual transport path simultaneously, by applying magnetic move forces to the sample container carriers. In addition, the laboratory sample distribution system can comprise a number of position sensors and a position determination unit. The position sensors can be stationary arranged below the transport plane. A position sensor, in particular each of the position sensors, can have a sensing region or can define a sensing region and can have an electrical resistance. The electrical resistance, in particular a value of the electrical resistance, can dependent on a position of a sample container carrier, in particular of one of the sample container carriers, on the transport plane located in the sensing region. The position determination unit can be adapted to determine the positions of the sample container carriers on top of the transport plane by evaluating the electrical resistances, in particular the electrical resistance values, of the position sensors.

The sample containers may be designed as tubes made of glass or transparent plastic and may have an opening at an upper end. The sample containers may be used to contain, store and transport samples such as blood samples, urine samples or chemical samples. The transport plane may also be denoted as transport surface. The transport plane can support the sample container carriers, what may also be denoted as carrying the sample container carriers. The electro-magnetic actuators may be solenoids surrounding ferromagnetic cores. Furthermore, the electro-magnetic actuators may be driven or energized individually in order to generate or to provide a magnetic field. The magnetic field may interact with the magnetically active device of a respective sample container carrier. By the interaction, the electro-magnetic actuator/s may apply the magnetic move force to the sample container carrier. Hence, the transport carrier may be translationally moved on the transport plane. For that purpose, the magnetically active device of the sample container carrier may be a permanent magnet. Alternatively or additionally, an electro-magnet and/or any magnetically soft material may be used. The sample container carriers may be adapted to move in two dimensions on the transport plane. For that purpose, the electro-magnetic actuators may be arranged in two dimensions, in particular, in a grid or matrix having rows and columns along which the electro-magnetic actuators can be arranged. The electro-magnetic actuators may be arranged in a plane parallel to the transport plane.

The position sensors and the position determination unit can enable improved sample container carrier position detection on the transport plane. The sensing region may extend only in one direction or in one dimension on the transport plane and/or may comprise a sensing line or sensing stripe on the transport plane. Then, the position sensor may have only the one electrical resistance with its value in the one direction. Alternatively, the sensing region may extend in two directions being different from each other or in two dimensions on the transport plane and/or may comprise a sensing area on the transport plane. Then, the position sensor may have the one electrical resistance with two values in the two directions. In other words, the position sensor may have two electrical resistances, each with a value in its direction. The sensing region may be limited, such that, when the sample container carrier may be located out or outside of the sensing region, the electrical resistance may not be dependent on the position of the sample container carrier on the transport plane. In this case, the electrical resistance may have a default value, e.g. a zero value or an extreme value. The electrical resistance and its value/s, respectively, may be unambiguously assigned or correlated to the position of the sample container carrier on the transport plane located in the sensing region. Hence, the position of the sample container carrier on the transport plane located in the sensing region may be unambiguously determined by the position determination unit. This can be an advantage to a Hall-sensor, which in contrast to the case of a one-dimensional sensing region, can have two points, for which the Hall-sensor can give the same Hall-voltage such that the two points cannot be distinguished. In the case of a two-dimensional sensing region, the Hall-sensor can have a lot of points on a shared circle, for which the Hall-sensor can give the same Hall-voltage and thus cannot be distinguished. The electrical resistance may be evaluated or measured by applying a voltage to the electrical resistance in one direction and by measuring a resulting electric current in the same direction. The electrical resistance may also be denoted as longitudinal electrical resistance. The position sensors may be arranged next or adjacent to each other along the transport plane, in particular such that the sensing regions of neighboring position sensors may not overlap or may overlap only partially, e.g. maximum ten percent in one dimension. From the known positions of the positions sensors below the transport plane and the evaluation of their electrical resistances and their values, respectively, the positions of the sample container carriers on top of the transport plane may be determined by the position determination unit.

According to an embodiment, the position sensor can comprise a spatially deflectable element. A spatial deflection of the spatially deflectable element can be dependent on the position of the sample container carrier located in the sensing region. The electrical resistance can be dependent on the spatial deflection. The spatial deflection may be along and/or substantially perpendicular to the transport plane. In particular, the spatially deflectable element may follow the sample container carrier along the transport plane and/or correspond to its position. The spatial deflection perpendicular to the transport plane may occur at and below, respectively, the position of the sample container carrier on the transport plane and not elsewhere. In particular, the spatially deflectable element may be deflected between at least two deflection states. When the sample container carrier is located out of the sensing region, no spatial deflection may occur, the spatially deflectable element may be deflected into a default deflection state and/or the spatially deflectable element may stay in its last state.

According to an embodiment, the spatially deflectable element can comprise a magnetic material. The magnetic material can be adapted to interact or interacts with the magnetically active device of the sample container carrier located in the sensing region such that the spatial deflection can be caused. The magnetic material may comprise permanent magnetic material and/or magnetically soft material such as, for example, iron. Advantageously, the magnetically active device of the sample container carrier may be a permanent magnet and/or an electro-magnet, when the magnetic material can comprise magnetically soft material, or the magnetic material may comprise permanent magnetic material, when the magnetically active device of the sample container carrier can comprise magnetically soft material.

According to an embodiment, the spatially deflectable element can be embodied as a flexible membrane. In one embodiment, the flexible membrane can extend along or substantially parallel to the transport plane. The flexible membrane may be spatially deflected perpendicular to the transport plane. The use of the flexible membrane may ensure a relatively high reliability of the position sensor since a relatively small and thereby relatively low-wear deflection of the flexible membrane may be sufficient to affect the electrical resistance.

According to an embodiment, the position sensor can have a given sensor length along the transport plane. The sensor length can define the sensing region. The electrical resistance can be dependent on the position of the sample container carrier on the transport plane located in the sensing region along the sensor length. In one embodiment, the position sensor may comprise a housing and the sensor length may be defined by the housing.

According to an embodiment, the sensor length can be in the range of about 20 millimeter (mm) to about 60 mm. In one embodiment, the sensor length can be in the range of about 30 mm to about 50 mm. The sample container carrier may have a diameter on the transport plane and/or may have a footprint on the transport plane in this range. By the selection of this sensor length range, on the one hand, the sensor length may be relatively small enough to ensure that only one sample container carrier may be located in the sensing region at a time. On the other hand, the sensor length may be relatively large enough to ensure that a relatively low number of position sensors may be sufficient to capture the whole transport plane.

According to an embodiment, the position sensor can comprise a resistance element. The resistance element can extend over the sensor length along the transport plane. In addition, the position sensor can comprise a conductance element. The conductance element can be adapted to make a position-changeable electrical contact with the resistance element such that the electrical resistance can be caused. A position of the electrical contact along the resistance element can be dependent on, in one embodiment; can correspond to, the position of the sample container carrier, in one embodiment, on the transport plane located in the sensing region along the resistance element. The position-changeable electrical contact may be present permanently, or only temporarily, when the sample container carrier is located in the sensing region. Furthermore, the position sensor may comprise a first electrical contact element, wherein the first electrical contact element may electrically contact the resistance element. Advantageously, the first electrical contact element may contact the resistance element at one end. The electrical resistance may be caused or established in between the conductance element and the first electrical contact element. This arrangement may also be denoted as variable resistor. In addition, the position sensor may comprise a second electrical contact element, wherein the second electrical contact element may electrically contact the resistance element. Advantageously, the second electrical contact element may contact the resistance element at an opposite end than the first electrical contact element. A voltage may be applied in between the first electrical contact element and the second electrical contact element. A resulting voltage drop may be evaluated or measured in between the conductance element and the first electrical contact element, wherein the voltage drop may be a measure for the electrical resistance. This arrangement may also be denoted as potentiometer or voltage divider. The conductance element may also be denoted as voltage tap.

According to an embodiment, the conductance element can extend over the sensor length along the transport plane such as, for example, along the resistance element.

According to an embodiment, the spatially deflectable element can be formed by the resistance element and/or the conductance element. The spatial deflection of the spatially deflectable element can cause the position-changeable electrical contact. In one embodiment, the resistance element and/or the conductance element may be embodied as the flexible membrane. Alternatively or additionally, the conductance element may be embodied as a sliding contact element, which may be adapted to slide along the resistance element.

According to an embodiment, the resistance element can extend in a first direction and in a second direction different from the first direction. In addition, the position sensor can comprise a multiplexer for determination of the electrical resistance in the first direction and in the second direction. The multiplexer may enable determination or to measurement of the electrical resistance in the first direction independent from the electrical resistance in the second direction. In one embodiment, the first direction may be substantially perpendicular to the second direction. Furthermore, the position sensor may comprise for each direction an electrical contact element and optionally another electrical contact element.

According to an embodiment, the position sensors can be arranged in rows and columns. The rows and columns may form a grid or matrix. Furthermore, the grid of the position sensors may correspond or be aligned to a grid of the electro-magnetic actuators. Moreover, the position sensors may be arranged in a plane parallel to the transport plane.

According to an embodiment, the position sensors can be arranged in between the transport plane and the electro-magnetic actuators.

According to an embodiment, the laboratory sample distribution system can comprise a printed circuit board. The printed circuit board can be stationary arranged below the transport plane. The position sensor, in particular, each of the position sensors, can be embodied as a surface-mount device and can be mounted directly onto a surface of the printed circuit board. Thereby, the position sensor/s may be easily installed or integrated below the transport plane.

According to an embodiment, the laboratory sample distribution system can comprise a control unit. The control unit can be in signal connection with the position determination unit. Also, the control unit can be configured to control the movements of the sample container carriers on top of the transport plane by driving the electro-magnetic actuators dependent on the positions of the sample container carriers on top of the transport plane such that the sample container carriers can move along corresponding transport paths.

A laboratory automation system is presented. The laboratory automation system can comprise a number of pre-analytical, analytical and/or post-analytical laboratory stations. In addition, the laboratory automation system can comprise a laboratory sample distribution system as described above. The laboratory sample distribution system can be adapted to distribute the sample container carriers and/or sample containers between the laboratory stations. The laboratory stations may be arranged adjacent to the laboratory sample distribution system.

Pre-analytical laboratory stations may be adapted to perform any kind of pre-processing of samples, sample containers and/or sample container carriers. Analytical laboratory stations may be adapted to use a sample or part of the sample and a reagent to generate a measuring signal, the measuring signal indicating if and in which concentration, if any, an analyte exists. Post-analytical laboratory stations may be adapted to perform any kind of post-processing of samples, sample containers and/or sample container carriers. The pre-analytical, analytical and/or post-analytical laboratory stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, a sealing/desealing station, a pushing station, a belt station, a conveying system station and/or a gripper station for moving the sample container to or from the sample container carrier.

By the laboratory sample distribution system, the advantages of the laboratory sample distribution system, as discussed above, can be made applicable for the laboratory automation system.

Referring initially to FIG. 1, FIG. 1 shows a laboratory sample distribution system 100. The laboratory sample distribution system 100 can comprise a transport plane 130 and a number of electro-magnetic actuators 140. The electro-magnetic actuators 140 can be stationary arranged below the transport plane 130. The electro-magnetic actuators 140 can be quadratically arranged in a grid having rows and columns in a plane substantially parallel to the transport plane 130. Furthermore, the electro-magnetic actuators 140 can be implemented as solenoids each having a solid ferro-magnetic core 145.

Moreover, the laboratory sample distribution system 100 can comprise a number of sample container carriers 110. The transport plane 130 can be adapted to support the sample container carriers 110. Each of the sample container carriers 110 can comprise a sliding surface on its underside. The sliding surfaces can be adapted to be in contact with the transport plane 130 and can enable movement of the sample container carriers 110 on the transport plane 130. The sample container carriers 110 can be positioned on the transport plane 130. While it can be understood that a plurality of sample container carriers 110 such as, for example, at least ten, at least one hundred or at least one thousand, can be positioned on the transport plane 130, due to simplicity only three sample container carriers are depicted in FIG. 1. Each of the sample container carriers 110 can be adapted to carry a sample container 120. Also, each of the sample container carriers 110 can comprise a magnetically active device 115, as depicted in FIG. 2, which can be in this embodiment a permanent magnet.

The electro-magnetic actuators 140 can be adapted to move the sample container carriers 110 on top of the transport plane 130 such that, for example, each of them along an individual transport path simultaneously, by applying magnetic move forces to the sample container carriers 110. In detail the electro-magnetic actuators 140 can be driven individually in order to generate a magnetic field for each sample container carrier 110. The magnetic field can interact with the magnetically active device 115 of the respective sample container carrier 110. By the interaction the electro-magnetic actuators 140 can apply the magnetic move force to the sample container carrier 110. Hence, the sample container carriers 110 can be translationally moved in two dimensions on the transport plane 130.

In addition, the laboratory sample distribution system 100 can comprise a number of position sensors 150 and a position determination unit 170. The position sensors 150 can be stationary arranged below the transport plane 130. Each of the position sensors 150 can have a sensing region 160 and an electrical resistance Rx, Ry. The electrical resistance Rx, Ry, in particular, a value of the electrical resistance Rx, Ry, can be dependent on a position PS of a sample container carrier 110 on the transport plane 130 located in the sensing region 160 of a respective position sensor 150. The position determination unit 170 can be adapted to determine the positions PS of the sample container carriers 110 on top of the transport plane 130 by evaluating the electrical resistances Rx, Ry, in particular, the electrical resistance values, of the position sensors 150.

In the shown embodiment, the sensing region 160 of each position sensor 150 can extend in two directions x, y substantially perpendicular to each other on the transport plane 130. In this case, the sensing region 160 can comprise a sensing area on the transport plane 130. Furthermore, each of the position sensors 150 can have an electrical resistance Rx and an electrical resistance value, respectively, for a first direction x and an electrical resistance Ry and an electrical resistance value, respectively, for a second direction y, as depicted in FIGS. 4b and 4c.

In detail, each of the position sensors 150 can have a given sensor length Lx in the first direction x along the transport plane 130 and a given sensor length Ly in the second direction y along the transport plane 130, as depicted in FIGS. 3 and 4a. The sensor lengths Lx, Ly can define the sensing region 160 of the respective position sensor 150. The electrical resistance Rx in the first direction x can be dependent on the position PS of the sample container carrier 110 on the transport plane 130 located in the sensing region 160 along the sensor length Lx. The electrical resistance Ry in the second direction y can be dependent on the position PS of the sample container carrier 110 on the transport plane 130 located in the sensing region 160 along the sensor length Ly. In the shown embodiment, each of the sensor lengths Lx, Ly can be about 40 mm. These sensor lengths can correspond to a diameter of each sample container carrier 110 on the transport plane 130.

Further, the position sensor 150 can comprise a resistance element 210. The resistance element 210 can extend over the sensor length Lx in the first direction x along or substantially parallel to the transport plane 130 and can extend over the sensor length Ly in the second direction y along or substantially parallel to the transport plane 130. In addition, the position sensor 150 can comprise a conductance element 220. The conductance element 220 can be adapted to make a position-changeable electrical contact 230 with the resistance element 210, such that the electrical resistances Rx, Ry can be caused. A position PC of the electrical contact 230 along the resistance element 210 can be dependent on the position PS of the sample container carrier 110 on the transport plane 130 located in the sensing region 160 along the resistance element 210.

Also, the position sensor 150 can comprise a spatially deflectable element 190. A spatial deflection of the spatially deflectable element 190 can be dependent on the position PS of the sample container carrier 110 located in the sensing region 160. The electrical resistances Rx, Ry can be dependent on the spatial deflection.

In the shown embodiment, the spatially deflectable element 190 can be formed by the conductance element 220. The spatial deflection of the spatially deflectable element 190 can cause the position-changeable electrical contact 230. The spatially deflectable element 190 and the conductance element 220, respectively, can be embodied as a flexible membrane. The conductance element 220 can extend over the sensor length Lx in the first direction x along or substantially parallel to the transport plane 130 and the resistance element 210 and can extend over the sensor length Ly in the second direction y along or substantially parallel to the transport plane 130 and the resistance element 210.

The position sensor 150 can comprise a housing 290. The resistance element 210 and the conductance element 220 can be arranged inside of the housing 290 substantially parallel to each other, separated by an air gap. The housing 290 can be arranged below the transport plane 130 with the resistance element 210 being closer to the transport plane 130 than the conductance element 220. The flexible membrane embodied conductance element 220 can be fixed, or clamped, at its border or edge to the housing 290.

The spatially deflectable element 190 and the conductance element 220, respectively, can comprise a magnetic material 200. The magnetic material 200 can be adapted to interact or interacts with the magnetically active device 115 of the sample container carrier 110 located in the sensing region 160, such that the spatial deflection can be caused. In the shown embodiment, the magnetic material 200 can comprise magnetically soft material in the form of iron beads, wherein the iron beads can be integrated into the flexible membrane.

In other embodiments, the spatially deflectable element may be formed by the resistance element. In particular, the resistance element may be embodied as a flexible membrane. Furthermore, a housing may be arranged with the conductance element being closer to the transport plane than the resistance element. Moreover, the resistance element may comprise a magnetic material, wherein the magnetic material may be adapted to interact or may interact with the magnetically active device of the sample container carrier located in the sensing region, such that a spatial deflection of the resistance element may be caused and the position-changeable electrical contact with the conductance element may be made.

In the shown embodiment, a magnetic strength of both, the magnetically active device 115 of the sample container carrier 110 and the magnetic material 200 of the spatially deflectable element 190, can be chosen such that the magnetic material 200 can be attracted by the magnetically active device 115 such that the conductance element 220 can be spatially deflected substantially perpendicular to the transport plane 130 towards the resistance element 210 into electrical contact with it, when the sample container carrier 110 on the transport plane 130 is located in the sensing region 160 of the position sensor 150, wherein the spatial deflection can occur at and below, respectively, the position PS of the sample container carrier 110 on the transport plane 130 and not elsewhere. Thereby, the position-changeable electrical contact 230 can be made at the position PC, which can correspond to the position PS of the sample container carrier 110. The spatially deflectable element can be in a first deflection state or electrical contact deflection state.

In detail, the resistance element 210 can comprise a resistance material, which can be uniform along the sensor lengths Lx, Ly. The position sensor 150 can comprise a first electrical contact element 236. The first electrical contact element 236 can electrically contact the resistance element 210 at an end, in FIG. 4a on the left. The electrical resistance Rx in the first direction x can be between the first electrical contact element 236 and the conductance element 220 with its position-changeable electrical contact 230. In addition, the position sensor 150 can comprise a conductance contact element 235. The conductance contact element 235 can electrically contact the conductance element 220. The conductance element 220 can comprise a conductance material, wherein an electrical resistance of the conductance element 220 and an electrical resistivity of the conductance material, respectively, can be negligibly or insignificantly small compared to an electrical resistance of the resistance element 210 and to an electrical resistivity of the resistance material, respectively. Thereby, an electrical resistance in between the conductance contact element 235 and the position-changeable electrical contact 230 can be negligibly or insignificantly small compared to the electrical resistance Rx. In addition, the position sensor 150 can comprise a second electrical contact element 238. The second electrical contact element 238 can electrically contact the resistance element 210 at an opposite end than the first electrical contact element 236, in FIG. 4a on the right. A given voltage can be applied in between the first electrical contact element 236 and the second electrical contact element 238, e.g. 3.3 Volts (V), in particular in the first direction x. A resulting voltage drop can be evaluated or measured analog in between the conductance contact element 235 and the first electrical contact element 236, in particular in the first direction x, wherein the evaluated voltage drop can be a measure for the electrical resistance Rx in the first direction x. This arrangement may also be denoted as potentiometer. The conductance element 220 may also be denoted as voltage tap. The electrical resistance Rx may also be denoted as longitudinal electrical resistance.

The position sensor 150 can comprise a third electrical contact element 237. The third electrical contact element 237 can electrically contact the resistance element 210 at an end, in FIG. 4a on the bottom. The electrical resistance Ry in the second direction y can be between the second electrical contact element 237 and the conductance element 220 with its position-changeable electrical contact 230. An electrical resistance in between the conductance contact element 235 and the position-changeable electrical contact 230 can be negligibly small compared to the electrical resistance Ry. In addition, the position sensor 150 can comprise a fourth electrical contact element 239. The fourth electrical contact element 239 can electrically contact the resistance element 210 at an opposite end than the third electrical contact element 237, in FIG. 4a on the top. The given voltage can be applied in between the third electrical contact element 237 and the fourth electrical contact element 239. A resulting voltage drop can be evaluated analog in between the conductance contact element 235 and the third electrical contact element 237, wherein the evaluated voltage drop can be a measure for the electrical resistance Ry in the second direction y. The electrical resistance Ry may also be denoted as longitudinal electrical resistance.

The position sensor 150 can comprise a multiplexer 240 for determination of the electrical resistance Rx, Ry in the first direction x and in the second direction y. Firstly, the given voltage can be applied between the first electrical contact element 236 and the second electrical contact element 238 by the multiplexer 240 and the electrical resistance Rx can be determined, while no voltage is applied between the third electrical contact element 237 and the fourth electrical contact element 239. Secondly, the given voltage can be applied between the third electrical contact element 237 and the fourth electrical contact element 239 by the multiplexer 240 and the electrical resistance Ry can be determined, while no voltage is applied between the first electrical contact element 236 and the second electrical contact element 238. Thereby, the multiplexer 240 can determine or measure the electrical resistance Rx in the first direction x independent from the electrical resistance Ry in the second direction y.

The electrical resistances Rx, Ry can be unambiguously assigned to the position PS of the sample container carrier 110 on the transport plane 130 located in the sensing region 160 of the respective position sensor 150. The electrical resistance Rx in the first direction x can increase with the position-changeable electrical contact 230 moving from the left to the right in FIG. 4a. The electrical resistance Ry in the second direction y can increase with the position-changeable electrical contact 230 moving from the bottom to the top in FIG. 4a. For the position PS of the sample container carrier 110 shown in FIGS. 3 and 4, the electrical resistance Rx can be larger than the electrical resistance Ry and both can be almost at maximum. Hence, the position PS of the sample container carrier 110 located in the sensing region 160 of the respective position sensor 150 can be unambiguously determined by the position determination unit 170. When the sample container carrier 110 is located outside of the sensing region 160 of the respective position sensor 150, no spatial deflection of the spatially deflectable element 190 and the conductance element 220, respectively, can occur. The spatially deflectable element 190 can be in a second deflection state or default deflection state. The position-changeable electrical contact 230 may not be present. In this case, the electrical resistances Rx, Ry can each have an extreme value.

As depicted in FIG. 1, the position sensors 150 can be arranged in rows 250 and columns 260 such as, for example, quadratically. The rows and columns can form a grid. Furthermore, the grid of the position sensors 150 can correspond or can be aligned to the grid of the electro-magnetic actuators 140. The sensing regions 160 of neighboring position sensors 150 may not overlap, but can be seamlessly adjoined. Thereby, the whole transport plane 130 can be captured. From the known positions of the positions sensors 150 below the transport plane 130 and the evaluation of their electrical resistances Rx, Ry, the positions PS of the sample container carriers 110 on top of the transport plane 130 can be determined by the position determination unit 170. Moreover, the position sensors 150 can be arranged in between the transport plane 130 and the electro-magnetic actuators 140 such as, for example, in a plane substantially parallel to the transport plane 130, as depicted in FIG. 5.

Further, the laboratory sample distribution system 100 can comprise a printed circuit board 270. The printed circuit board 270 can be stationary arranged below the transport plane 130. Each of the position sensors 150 can be embodied as a surface-mount device and can be mounted directly onto a surface 280 of the printed circuit board 270.

In addition, the laboratory sample distribution system 100 can comprise a control unit 180, as depicted in FIG. 1. The control unit 180 can be in signal connection with the position determination unit 170. In addition, the control unit 180 can be configured to control the movements of the sample container carriers 110 on top of the transport plane 130 by driving the electro-magnetic actuators 140 dependent on the positions PS of the sample container carriers 110 on top of the transport plane 130 such that the sample container carriers 110 can independently and simultaneously move along the transport paths.

The laboratory sample distribution system 100 can be part of a laboratory automation system 10. The laboratory automation system 10 can comprise the laboratory sample distribution system 100 and a number of pre-analytical, analytical and/or post-analytical laboratory stations 20 arranged adjacent to the laboratory sample distribution system 100. Self-evidently, more than the two laboratory stations 20 depicted in FIG. 1 may be comprised in the laboratory automation system 10. The laboratory sample distribution system 100 can be adapted to distribute the sample container carriers 110 and/or the sample containers 120 by the sample container carriers 110 between the laboratory stations 20. The laboratory stations 20 can be positioned adjacent to the transport plane 130 such that the sample container carriers 110 can be used to transport the sample containers 120 or its content to it.

As the shown and above discussed embodiments reveal, a laboratory sample distribution system comprising a number of sample container carriers, a transport plane, a number of electro-magnetic actuators, a number of position sensors and a position determination unit can be provided. The position sensors and the position determination unit can enable improved sample container carrier position detection on the transport plane. Furthermore, a laboratory automation system comprising such a laboratory sample distribution system can be provided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a number of sample container carriers, wherein each of the sample container carriers comprises at least one magnetically active device and wherein each of the sample container carriers is adapted to carry at least one sample container;
   a transport plane, wherein the transport plane is adapted to support the sample container carriers;
   a number of electro-magnetic actuators, wherein the electro-magnetic actuators are stationary arranged below the transport plane and wherein the electro-magnetic actuators are adapted to move the sample container carriers on top of the transport plane by applying magnetic move forces to the sample container carriers;
   a number of position sensors, wherein the position sensors are stationary arranged below the transport plane and wherein a position sensor has a sensing region and has an electrical resistance (Rx, Ry), wherein the electrical resistance is dependent on a position (PS) of a sample container carrier on the transport plane located in the sensing region, wherein the position sensor has a given sensor length (Lx, Ly) along the transport plane, wherein the sensor length defines the sensing region, and wherein the electrical resistance (Rx, Ry) is dependent on the position (PS) of the sample container carrier on the transport plane located in the sensing region along the sensor length, wherein the position sensor comprises a resistance element, wherein the resistance element extends over the sensor length (Lx, Ly) along the transport plane, and a conductance element, wherein the conductance element is adapted to make a position-changeable electrical contact with the resistance element such that the electrical resistance (Rx, Ry) is caused, and wherein a position (PC) of the electrical contact along the resistance element is dependent on the position (PS) of the sample container carrier; and
   a position determination unit, wherein the position determination unit is adapted to determine the positions of the sample container carriers on top of the transport plane by evaluating the electrical resistances of the position sensors.

2. The laboratory sample distribution system according to claim 1, wherein the sensor length (Lx, Ly) is in the range from 20 mm to 60 mm.

3. The laboratory sample distribution system according to claim 1, wherein the conductance element extends over the sensor length (Lx, Ly) along the transport plane.

4. The laboratory sample distribution system according to claim 1, wherein the spatially deflectable element is formed by the resistance element and/or the conductance element and wherein the spatial deflection of the spatially deflectable element causes the position-changeable electrical contact.

5. The laboratory sample distribution system according to claim 1, wherein the resistance element extends in a first direction (x) and in a second direction (y) being different from the first direction and wherein the position sensor comprises a multiplexer for determination of the electrical resistance in the first direction (Rx) and in the second direction (Ry).

6. The laboratory sample distribution system according to claim 1, wherein the position sensors are arranged in rows and columns.

7. The laboratory sample distribution system according to claim 1, wherein the position sensors are arranged in between the transport plane and the electro-magnetic actuators.

8. The laboratory sample distribution system according to claim 1, further comprising,
a printed circuit board, wherein the printed circuit board is stationary arranged below the transport plane and wherein the position sensor is embodied as a surface-mount device and is mounted directly onto a surface of the printed circuit board.

9. The laboratory sample distribution system according to claim 1, further comprising,
a control unit, wherein the control unit is in signal connection with the position determination unit and wherein the control unit is configured to control the movements of the sample container carriers on top of the transport plane by driving the electro-magnetic actuators dependent on the positions (PS) of the sample container carriers on top of the transport plane such that the sample container carriers move along corresponding transport paths.

10. A laboratory automation system, the laboratory automation system comprising:
a number of a pre-analytical, analytical and/or post-analytical laboratory stations; and
a laboratory sample distribution system according to claim 1, wherein the laboratory sample distribution system is adapted to distribute the sample container carriers and/or sample containers between the laboratory stations.

11. The laboratory sample distribution system according to claim 1, wherein the position sensor comprises a spatially deflectable element, wherein a spatial deflection of the spatially deflectable element is dependent on the position (PS) of the sample container carrier located in the sensing region, and wherein the electrical resistance (Rx, Ry) is dependent on the spatial deflection.

12. The laboratory sample distribution system according to claim 11, wherein the spatially deflectable element comprises a magnetic material, wherein the magnetic material is adapted to interact with the magnetically active device of the sample container carrier located in the sensing region such that the spatial deflection is caused.

13. The laboratory sample distribution system according to claim 11, wherein the spatially deflectable element is embodied as a flexible membrane.

14. The laboratory sample distribution system according to claim 13, wherein the flexible membrane extends along the transport plane.

* * * * *